US006100452A

United States Patent [19]
Langham

[11] Patent Number: 6,100,452
[45] Date of Patent: Aug. 8, 2000

[54] METHOD FOR MAKING NON-DEHISCENT SESAME

[75] Inventor: Derald Ray Langham, San Antonio, Tex.

[73] Assignee: Sesaco Corporation, Paris, Tex.

[21] Appl. No.: 09/150,799

[22] Filed: Sep. 10, 1998

[51] Int. Cl.$^7$ .............................. A01H 5/00; A01H 5/10; A01H 1/04
[52] U.S. Cl. ........................................... 800/298; 800/260
[58] Field of Search .................................. 800/298, 260, 800/258

[56] References Cited

PUBLICATIONS

Bakheit et al. Inheritance of some qualitative and quantitative characters in sesame, *Sesamum indicum* L. AssiutJournal of Agricultural Sciences. vol. 27, pp. 27–41, 1996.
Delgado et al. Dilallel cross analysis of six indehiscent and two dehiscent varieties of sesame. Agronomia Tropical, vol. 42, pp. 191–210, 1992.
Langham, D.G., "Natural and Controlled Pollination in Sesame", *Journal of Heredity*, vol. XXXV, No. 8, pp. 254–256 (1944).
Langham, D.G., Rodriguez, Maximo, "Improvement of Sesame in Venezuela", Proceedings of 1st International Sesame Conference, Clemson, S.C., pp. 74–79 (1949).
Kalton, Robert R., "Sesame, A Promising New Oilseed Crop for Texas", Proceedings of 1st International Sesame Conference, Clemson, S.C., pp. 62–66 (1949).
Langham,D.G., Rodriquez, Maximo, and Reveron Esteban, "Dehiscencia y otras características del ajonjolí, *Sesamum indicum* L., en relación con el problema de la cosecha", Genesa, Maracay, Venezuela, pp. 3–16 (1956).
Langham, D. Ray, "Shatter Resistance in Sesame", Report presented at Induced Mutations for Sesame Improvements meeting, Apr. 6–10, 1998 in Bangkok, Thailand, 14 pages.
Shigeo, M., Hiroyuki, S. and Yumi, K., "Breeding of good quality sesame with dehiscence resistance and strong antioxidative property", Baiorunessansu Keikaku (Abstract) (1994).
Osman, H.E., "Studies in Sesame: Hybridization and Related Techniques", FAO Plant Production and Protection Paper No. 66, pp. 145–156 (1985).
Weiss, E.A., "History", *Castor, Sesame, and Safflower*, Chapter 12, Leonard Hill Books, London, pp. 311–525 (1971).
Yermanos, D.M., "Sesame", Chapter 39, *Hybridization of Crop Plants*, American Society of Agromomy–Crop Science of America, pp. 549–563 (1980).
Weiss, E.A., "Sesame", Chapter 7, *Oilseed Crops,* Longman, London, pp. 282–340 (1983).
Hutson, B.D., "Standards for the Inspection and Grading of Sesame Seed", Hutson Laboratories, Yuma, Arizona pp. 1–5 (1983).
Yermanos, D.M., "Sesame Growing: An Idealized Overview", Text of speech given in Cairo, Egypt, 4 pages, (1984).
Ashri, A., "Sesame", Chapter 18, *Oil Crops of the World*, pp. 375–387 (1989).
"Recommendations of the Discussion Groups", Proceedings of Sesame Workshop, Mar. 21–23, 1995, pp. 252–257.
Zanten, L. van (ed), Conclusions and Recommendations, Report of the 2nd FAO.IAEA Research Coordination Meeting, Antalya, Turkey, pp. 107–113 (1997).
Day, Jamie, "The mechanism of indehiscence in sesame. Features that might be useful in a breeding program.", Paper presented at Induced Mutations for Sesame Improvements meeting,, Bangkok, Thailand, 11 pages (1998).

*Primary Examiner*—Lynette R. F. Smith
*Assistant Examiner*—Melissa L. Kimball
*Attorney, Agent, or Firm*—Sidley & Austin

[57] ABSTRACT

A breeding method for a non-dehiscent sesame plant has been developed. Non-dehiscent sesame varieties are characterized by having sufficient capsule split, capsule opening, capsule placenta attachment, capsule constriction, and capsule membrane attachment to allow seed retention in the field after physiological maturity during adverse weather conditions such as rain, wind, and dew and also to allow ready release of seed from the capsule during mechanized harvesting with minimal broken seed. A mechanical method is also provided for quantitative screening of sesame plants for non-dehiscence.

46 Claims, 8 Drawing Sheets

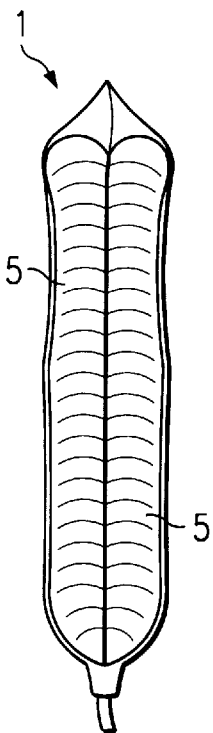
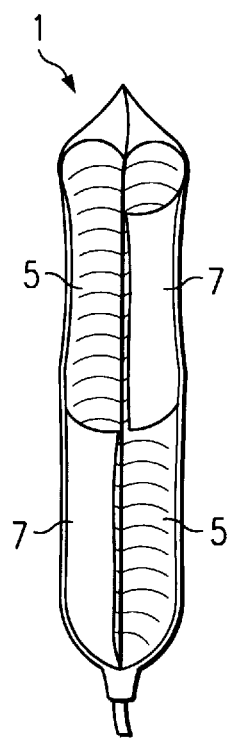
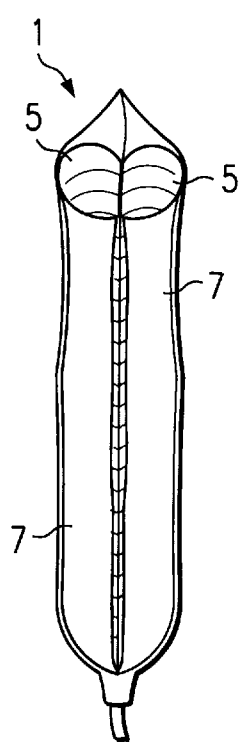
FIG. 4A          FIG. 4B          FIG. 4C
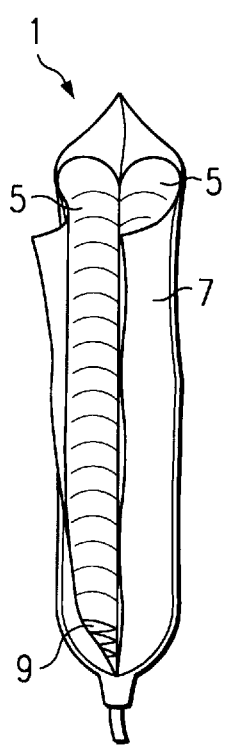
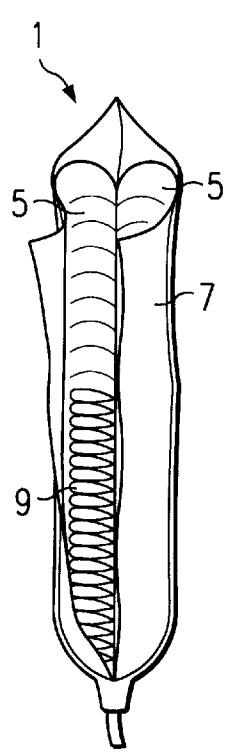
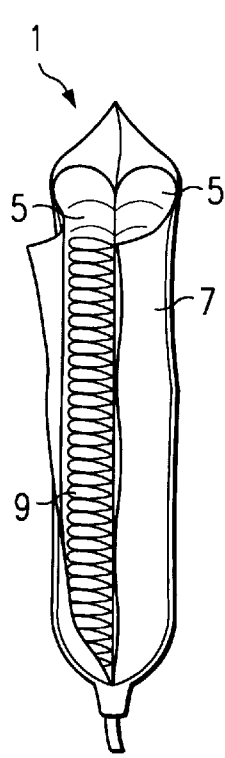
FIG. 5A          FIG. 5B          FIG. 5C

```
                                    /SOMALIA
                              /FLXL
                       /FLXL   \118
                        |   |   /193
                        |   \FLXL    /MAXIMO
                        |       \076         /R234
                        |                \R234 TALL
              /FLXL                              \BEE
               |   |              /G8
               |   |           /045
               |   |    /FLXL   \958
               |   |    |   |
               |   |    |   |   /982
               |   |    |   \036
               |   \FLXL        \G53.80-1
               |           |     /192
               |           |    /195
               |           \FLXL    \BEE
               |                \701
              /FXA
               |   |   /G8
               |   \S11    /111
               |       \111X
               |           \BEE
              /FAB
               |   |   /G8
               |   \S11    /111
               |   |   \111X
       11W     |        \BEE
               |    /G8
               |   /S11    /111
               |   |   \111X
               |   |       \BEE
               \S17    /702
                   \72A
                       \BEE
```

*FIG. 10*

```
            /G8
         /804
       |     |      /111
    /56B     \111X
     |   |          \BEE
     |   |
     |   |          /111
     |   |      /F822
     |   \562       \192
19A          \700
  |
  |          /192
  |      /855
  |   |       \104
   \55A
       |     /G8
       \S11       /111
              \111X
                  \BEE
```

*FIG. 12*

METHOD FOR MAKING NON-DEHISCENT SESAME

TECHNICAL FIELD OF THE INVENTION

This invention concerns sesame plant breeding and providing sesame plant varieties appropriate for mechanized harvesting.

BACKGROUND OF THE INVENTION

Sesame, or *Sesamum indicum*, is a tropical annual cultivated for its oil and its nut flavored seeds. The sesame plant grows to a height of 2–7 feet, and at its leaf axils are found capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual nonmechanized methods, it is desirable for the sesame seed to fall readily from the plant. Upon physiological maturity, the sesame stalks are cut, tied into small bundles, and then stacked in shocks. Further harvesting procedures vary from country to country and from area to area within countries. Some move the shocks to a threshing floor so that the seed that falls out can be recovered. Others put plastic or cloth in the fields under the shocks to catch the seed. For manual harvesting methods in which the dried, shocked sesame is moved to a threshing floor or over a plastic or cloth, preferred plant varieties include dehiscent, or super shattering, in which less than 10% of the seeds set are retained in the capsule.

Other methods involve leaving the shocks in the fields, and when the shocks are dry, the sesame is turned upside down and struck with an implement to shake out all of the seed. For this type of manual harvesting method, it is preferred that the capsule hold as much of the sesame seed as possible until the farmer inverts the stalk. Plant varieties rated as shattering which retain as much seed as possible before inversion are preferred. Common methods of manual harvest are discussed in Weiss, E. A., (1971). *Castor, Sesame, and Safflower*. Leonard Hill Books, London, England.

In an effort to mechanize the harvest of sesame, D. G. Langham introduced the use of swathers in Venezuela in 1944. The swathers were used to cut the sesame plants, manual labor was used to bundle and shock the cut plants, and combines were brought in to thrash the shocks. It was determined that seed shattering during mechanized harvesting methods caused considerable loss of sesame seed. While mechanization was considered to be essential for crop production in the Western hemisphere, it became obvious that the dehiscence of the sesame seed pod was the principal obstacle to the widespread acceptance of sesame as a commercial crop. (Langham, D. G. 1949. "Improvement of Sesame in Venezuela," *Proceedings First International Sesame Conference*, Clemson Agricultural College, Clemson, S.C., pp. 74–79). As programs to introduce sesame production in the United States in Arizona, South Carolina, Nebraska, Oklahoma, and Texas were initiated, mechanization was considered essential due to high labor costs. Kalton, one of the Texas researchers, reported that the shattering nature of available strains was the main obstacle in complete mechanization of the sesame crop. (Kalton, R. 1949. "Sesame, a promising new oilseed crop for Texas," *Proc First International Sesame Conference*, Clemson Agricultural College, Clemson, S.C., pp. 62–66).

In 1943, D. G. Langham found a mutation on a sesame plant. Capsules did not open on plants expressing this mutation (FIG. 8). In succeeding generations, Langham showed that it was a recessive single gene which produced this indehiscence, where all the seeds were retained inside the unopened capsule. While it was believed that indehiscence would solve the problem of seed loss on mechanized harvesting, it was found that the capsules were too tough to effectively release the seed. Many of the capsules passed through a combine without opening. When more rigorous combining was attempted, an increase in efficiency of capsule opening was achieved but at the expense of seed quality. Seeds were broken due to the more rigorous combine conditions, and the broken seeds released free fatty acids. Chemical reactions with free fatty acids led to rancidity and concomitant undesirability of the harvested seed.

The indehiscent sesame varieties described above were used by various plant breeders in an attempt to develop desirable sesame lines. In addition to traditional cross-breeding approaches, some attempted to alter the chromosome numbers through tetraploids and interspecific crosses. Yermanos attempted to improve release of seed by increasing the length of the capsule so that there would be more surface for the combine to crack the capsules open (personal communication). Unfortunately, even with a small opening on the top of the capsule, a high percentage of broken seed was found on mechanized harvesting, preventing commercial use of this sesame line.

D. G. Langham reported in the late 1950's that the placenta attachment between each sesame seed and the placenta was important in the retention of seed in the capsule. He believed that he could improve the shatter resistance of sesame with increased placenta attachment but did not believe that all the seed could be retained in the capsule. However, Yermanos reported that during capsule maturity, the placenta attachment gradually weakens and is obliterated when the capsule is completely desiccated. (Yermanos, D. M. 1980. "Sesame. Hybridization of crop plants," *Am Soc Agronomy-Crop Sci of America*, pp. 549–563). Thus, it appeared that the placenta attachment would have little effect on seed retention in dry, mature capsules during harvesting. A seamless gene which retained all the seed in the capsules was discovered by D. G. Langham and D. R. Langham in 1986 (FIG. 9). This was crossed with shattering types, and some progeny had an opening at the tip of the capsule. The seamless capsules were similar to the indehiscent capsules in that it was too difficult to remove the seed from the capsule without damaging the seed.

In 1982, the first non-shattering line (retaining 50–70% of the seeds set) requiring no manual labor was introduced. This line could be harvested by swathing the sesame, leaving it to dry in the field, and then picking it up by a combine. Although complete mechanization was achieved, extensive loss of seed due to adverse weather conditions continued to occur.

Other varieties were developed between 1988 and 1997 which allowed for direct combining with 70–90% seed retention, but extensive loss of seed due to wind and rain continued to occur. Lines that generally yielded 80% of the seed under ideal conditions would yield only 45–65% under adverse conditions. Thus, while many of the crosses began to moderate the deleterious effects of mechanized harvesting, none were able to increase the yields to the level of manually harvesting shattering cultivars.

New lines of sesame have now been discovered which are defined by a new category of dehiscence: non-dehiscence. These lines retain most of the seed within the capsule despite adverse weather conditions such as wind and rain. The sesame lines of the present invention retain a sufficient amount of sesame seed during mechanized harvesting to be competitive with manual harvesting. The invention permits mechanized harvesting to be used with minimization of seed breakage because extensive combining is not required to obtain practical yields. Thus, the invention permits reduction of manual labor and concomitant economical and more rapid harvesting of sesame seed as a commercial crop.

SUMMARY OF THE INVENTION

In one aspect, the present invention relates to non-dehiscent sesame plants characterized by having greater than or equal to about 65% of the total amount of sesame seed retained in unharvested capsules subjected to the shaker test, less than or equal to about 10% of the total amount of sesame seed retained in mechanically harvested capsules, and less than or equal to about 3% of the total amount of sesame seed which is released from capsules broken during mechanical harvesting.

In another aspect, the present invention relates to non-dehiscent sesame plants characterized by having greater than or equal to about 65% of the total amount of sesame seed retained in unharvested capsules subjected to the shaker test, less than or equal to about 5% of the total amount of sesame seed retained in mechanically harvested capsules, and less than or equal to about 7% of the total amount of sesame seed which is released from capsules broken during mechanical harvesting.

In another aspect, the present invention relates to non-dehiscent sesame plants characterized by having greater than or equal to about 65% of the total amount of sesame seed retained in unharvested capsules subjected to the shaker test, less than or equal to about 5% of the total amount of sesame seed retained in mechanically harvested capsules, and less than or equal to about 3% of the total amount of sesame seed which is released from capsules broken during mechanical harvesting.

In another aspect, the present invention relates to seeds and progeny of non-dehiscent sesame plants.

In yet another aspect, the present invention relates to a non-dehiscent sesame plant characterized by a capsule opening that is slightly to barely open, and a good to moderate capsule placenta attachment.

In yet another aspect, the present invention relates to a non-dehiscent sesame plant characterized by capsule split, capsule opening, capsule membrane completeness, capsule constriction, capsule membrane attachment, and capsule placenta attachment.

In yet another aspect, the present invention relates to a non-dehiscent sesame plant selected from the sesame lines Sesaco 22 (S22), Sesaco 23 (S23), Sesaco 24 (S24), 19A, and 11W, representative seed of said S22, S23, S24, 19A, and 11W having been deposited under ATCC accession number PTA-1400, PTA-1401, PTA-1402, PTA-1399, and PTA-1398 respectively.

In another aspect, the invention relates to seeds and progeny of non-dehiscent sesame plants derived from the sesame lines S22, S23, S24, 19A, and 11W.

In yet another aspect, the present invention relates to a non-dehiscent sesame plant having the same non-dehiscent phenotype as a plant selected from the sesame lines S22, S23, S24, 19A, and 11W.

In yet another aspect, the present invention relates to seeds and progeny derived from a non-dehiscent sesame plant having the same non-dehiscent phenotype as a plant selected from the sesame lines S22, S23, S24, 19A, and 11W.

In one aspect, the present invention relates to a method of breeding a non-dehiscent sesame by combining shatter resistant characteristics of capsule split, capsule opening, capsule membrane completeness, capsule constriction, capsule membrane attachment, and capsule placenta attachment.

In another aspect, the present invention relates to seeds produced according to the sesame breeding method for non-dehiscence.

In yet another aspect, the present invention relates to progeny plants produced according to the sesame breeding method for non-dehiscence.

In yet another aspect, the present invention relates to a method for screening sesame plant varieties for non-dehiscence.

In yet another aspect, the present invention relates to a sesame plant identified by the non-dehiscent screening test.

BRIEF DESCRIPTION OF THE DRAWINGS

FIG. 1A depicts a side view of the capsule (6) along the suture (2), further illustrating the two carpels (1), placenta (3), tip (4), and seed chamber (5).

FIG. 1B depicts a front view of the capsule (6).

FIG. 1C depicts front view of a carpel (1), or one half of a capsule split along the suture, further illustrating the placenta (3), membrane (7), locule (8), and seed (9).

FIG. 1D depicts a cross section of a capsule as it appears twenty-five days after fertilization, illustrating the carpel (1), suture (2), placenta (3), seed chamber (5), capsule (6), seed (9), placenta attachment (10), endocarp (11), epidermis (12), and mesocarp (13).

FIG. 2A depicts capsule split rated as TS1, with the capsule split almost to the base of the seed chamber.

FIG. 2B depicts capsule split rated as TS4, with the capsule split to the middle of the seed chamber.

FIG. 2C depicts capsule split rated as TS7, with the capsule split near the top of the seed chamber.

FIG. 3A depicts capsule opening rated as TO1, with the capsule opening near the bottom of the seed chamber.

FIG. 3B depicts capsule opening rated as TO4, with the capsule opening to the middle of the seed chamber.

FIG. 3C depicts capsule opening rated as TO7, with the capsule opening near the top of the seed chamber.

FIG. 4A–FIG. 4C depict capsule membrane completeness (TM), characterized by at least one section of the membrane (7) missing, thus exposing the seed chamber (5). Capsule membrane completeness is scaled as TM0 representing capsule membrane completeness of 0%, TM7 representing capsule membrane completeness of 100%, and TM4 representing capsule membrane completeness of 50%. The figures depict one of the two carpels, thus showing only half of the membranes. The membranes on the other carpel not shown may or may not reflect the membrane missing in the same location or the same amount of missing membrane. The rating reflects the amount of completion of all membranes on the two carpels. FIG. 4A depicts capsule membrane completeness rated as TM0, with the capsule membrane missing.

FIG. 4B depicts a capsule membrane completeness rated as TM4, with half of the capsule membrane complete.

FIG. 4C depicts capsule membrane completeness rated as TM7, with all of the capsule membrane complete but with the typical hole at the top.

FIG. 5A–FIG. 5C depict capsule constriction (TC), characterized by the amount of seed (9) remaining in the capsule's seed chamber (5) after the placenta is removed. In these drawings, the membrane (7) is pulled back on the left side to show the seed remaining. Capsule constriction is scaled as TC0 representing no capsule constriction, TC8 representing complete capsule constriction, and TC4 representing medium capsule constriction. FIG. 5A depicts capsule constriction rated as TC1, with few seeds remaining in the base.

FIG. 5B depicts medium capsule constriction rated as TC4, with half of the seeds present.

FIG. 5C depicts capsule constriction rated as TC7, with almost all of the seeds present.

FIG. 6A depicts capsule membrane attachment rated as TA1, with the capsule membrane attachment largely separated from the placenta.

FIG. 6B depicts a capsule membrane attachment rated as TA4, with the capsule membrane attachment about halfway to the placenta.

FIG. 6C depicts capsule membrane attachment rated as TA7, with the capsule membrane attachment almost to the placenta.

FIG. 7A depicts capsule placenta attachment rated as TP1, poor capsule placenta attachment.

FIG. 7B depicts a capsule placenta attachment rated as TP4, with moderate capsule placenta attachment.

FIG. 7C depicts capsule placenta attachment rated as TP7, with good capsule placenta attachment.

FIG. 7D depicts the attachment of the sesame seed (9) to the placenta (3) through the placenta attachment (10).

FIG. 8A depicts a front view of an indehiscent capsule along the suture.

FIG. 8B depicts a side view of an indehiscent capsule, illustrating the presence of a suture (2).

FIG. 9A depicts a front view of a seamless capsule.

FIG. 9B depicts a side view of a seamless capsule, illustrating the absence of a suture.

FIG. 10 is a crossing schematic for the 11W non-dehiscent sesame plant.

FIG. 12 is a crossing schematic for the 19A non-dehiscent sesame plant.

DETAILED DESCRIPTION OF THE INVENTION

Figure 1A:
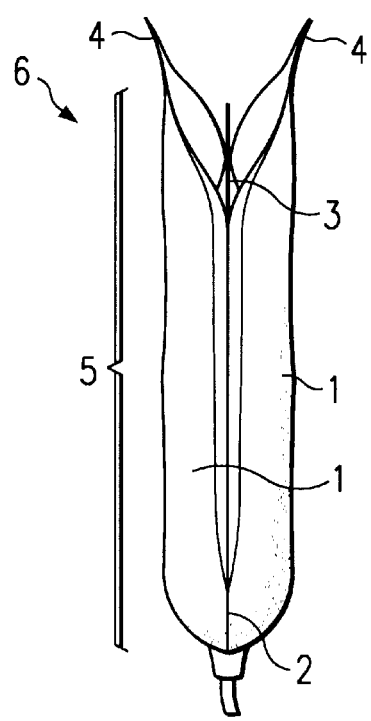
FIG. 1A–FIG. 1D depict the sesame capsule morphology and anatomy.
Figure 1B:
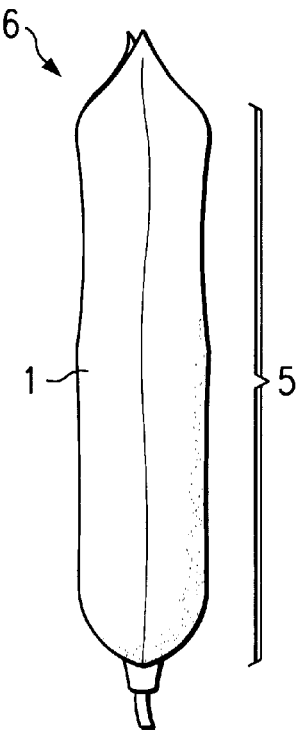
Figure 1C:
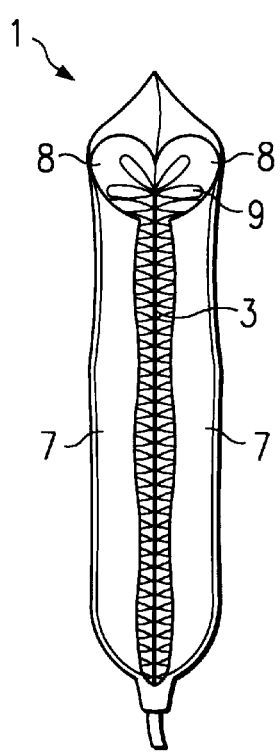
Figure 1D:
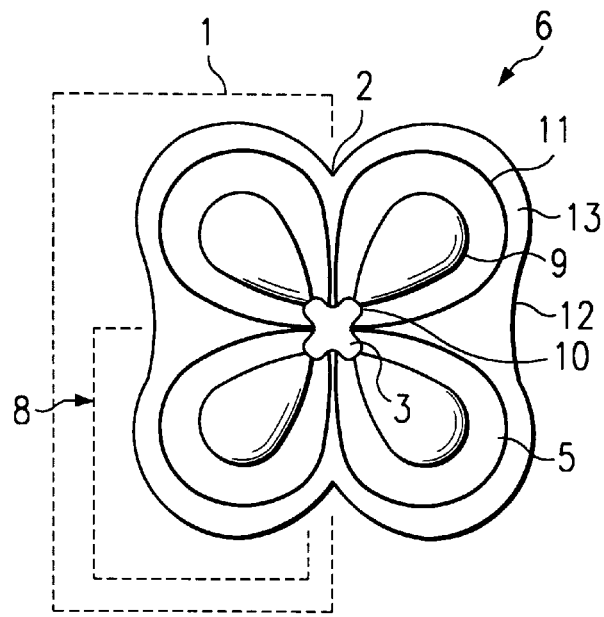

Novel non-dehiscent lines of sesame and methods for producing non-dehiscent lines have now been developed. In the method for producing non-dehiscent lines, the breeder following the teachings of the present invention may select appropriate sesame plants to cross with other sesame plants to result in progeny sesame plants having the desired characteristics of capsules to allow for better retention and less breakage of sesame seed during mechanized harvesting despite exposure of the sesame crop to adverse weather conditions such as rain and wind. These non-dehiscent lines provide for the first time a means by which commercially acceptable sesame seed can be mechanically harvested at a production rate comparable to manual harvesting regardless of weather conditions.

Non-dehiscent sesame lines are a type of shatter resistant sesame identified by the amount of sesame seed retained in the mature, dry capsules. These lines must hold the sesame seeds in the mature, dry capsules on the plants in the field but must release the seeds within the combine as easily as possible without breakage of the seeds. As used herein, "broken" sesame seed is defined as large and small pieces of kernels of sesame seed which have been broken and which remain in the harvested sample after the removal of dockage (*Standards for Inspection and Grading of Sesame Seed*, Hudson Laboratories, Nov. 1, 1993). The amount of seed retention is influenced by diverse characters of mature capsules which are manipulated through the present inventive method of breeding and selection processes to achieve non-dehiscence. It has been found that sesame plants phenotypically expressing only one of these characters does not have enough shatter resistance to qualify as non-dehiscent. However, in the method of the invention, multiple phenotypic characters become expressed in progeny plants and these multiple phenotypic characters provide the progeny plants with the desired non-dehiscence. These characters with corresponding rating methodology are summarized in Table I.

Capsule Characters Affecting Non-dehiscence

Sesame seed is produced in capsules (FIG. 1) that are in the leaf axils of the plants. Each capsule consists of carpels, and each carpel normally has two locules or seed chambers. Most sesame in the Western Hemisphere is bicarpellate, but tricarpellate and quadricarpellate cultivars are found in Asia and Africa. There has been no attempt to add

TABLE I

Capsule Shatter Resistant Characteristics Used in Development of Non-dehiscent Lines

| Abbreviation | Characteristics of the capsule | Rating/value System |
|---|---|---|
| Capsule split (TS) | extent of split between the carpels exposing the membranes but not exposing seed | no split to complete split; scale of 0–8; 1 = split almost to base of the capsules, 4 = split halfway down capsule; 7 = barely split; 8 = no split; in capsules where there is a difference in split on each side of the capsule, the greater split measurement is taken |
| Capsule opening (TO) | extent of opening between the carpels with membranes opening enough to expose seed and/or seed chamber | no opening to complete opening; scale of 0–8; 1 = open almost to bottom of the capsule; 4 = open halfway down; 7 = barely open; 8 = no opening |
| Capsule membrane completeness (TM) | the amount of missing membranes the carpels | complete membrane to no membrane; scale of 0–8; 0 = no membrane, 1 = most membranes incomplete, 4 = half of membranes incomplete, 7 = complete membranes, 8 = membranes with no holes |
| Capsule constriction (TC) | degree of constriction of the capsule around the seeds as shown by the amount of seed remaining in the capsule after the placenta is removed | no constriction to good constriction; scale of 0–8; 1 = little seed, 4 = half the seed, 7 = most of the seed |
| Capsule membrane attachment (TA) | amount of separation between the membrane and placenta | large to small separation between the membrane and placenta; scale 0–8; 0 = no membrane, 1 = large separation, 4 = medium separation, and 7 = little separation |
| Capsule placenta attachment (TP) | strength of placenta attachment | no to good placenta attachment scale of 0–8; 1 = minimal placenta attachment, 4 = some placenta attachment, 7 = good placenta attachment | non-dehiscence to lines other than bicarpellate, but it is expected that non-dehiscent lines can be made in tricarpellate and quadricarpellate cultivars using this invention. Normally, there is one row of 15–22 seeds per locule. In the center of the capsule, there is a placenta that nourishes the seeds during growth through a placenta attachment. In a cross-section, the outer layer is the epidermis followed by multiple layers of mesocarp (rounded parenchyma cells) with the endocarp (heavily lignified sclerenchyma cells) surrounding the seeds. (Day, J. 1998. "The mechanism of indehiscence in sesame-features that might be useful in a breeding programme"; presented at Induced Mutations for Sesame Improvements meeting held Apr. 6–10, 1998 in Bangkok, Thailand). In splitting the capsule between carpels, the endocarp is between the seeds in the two carpels. This part of the endocarp is known as the membrane. Although there is no visible line on the epidermis between the carpels, the mesocarp layers are arrayed at a suture to allow a splitting between the carpels. The force of the splitting is provided by the drying of the mesocarp layers of the cells.

The rating system used for providing values to the characters related to shatter resistance is a 0–8 scale. A subjective scale is used instead of measurements since the capsules vary considerably in length and width. The expression of the character will also vary between capsules on the same plant and capsules on different plants. The 0–8 scale provides a subjective method of averaging observations in order to differentiate varying levels of shatter resistance. The ratings can be used to compare lines within a nursery in a given year, but do not necessarily apply across different locations and/or years. However, the relationships between lines remains constant across different locations and years. FIGS. 2A–2C, 3A–3C, 4A–4C, 5A–5C, 6A–6C, and 7A–7C show three levels of ratings for each character.

Capsule Split ("TS")

Figure 2A:
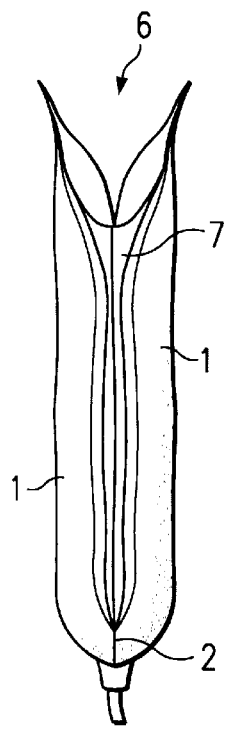
FIG. 2A–FIG. 2C depict capsule split (TS), characterized by a suture (2) exposing the membrane (7) but not the seeds and/or seed chamber. The drawings show a scale for measuring capsule split wherein TS0 represents capsule split to the bottom of the seed chamber, TS8 represents capsule split at the top of the seed chamber, and TS4 represents capsule split to the middle of the seed chamber.
Figure 2B:
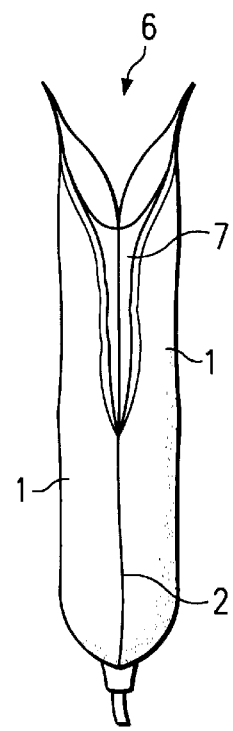
Figure 2C:
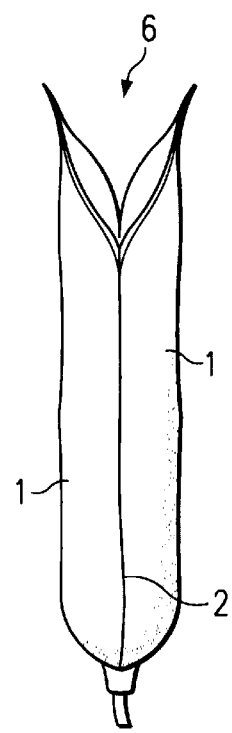

One of the characters of sesame found to be useful in breeding non-dehiscent sesame is related to splitting of the capsule which contains the sesame seeds in the mature plant (FIG. 2A–2C). Regardless of the degree of shatter resistance, most sesame lines follow the same sequence of capsule maturity. As a capsule matures, it begins to dry down, turning brown in the process. Usually after the capsule is brown, the tip of the capsule splits along the suture that eventually separates the carpels. The amount of capsule split is greatly affected by weather. In nature, capsules exhibiting characteristic capsule split will be open under dry conditions. During a heavy dew or rain, the capsules will close. If a fog or drizzle persists during the day, the capsules will remain relatively closed, but in the sun, they will open to a similar extent as found under dry conditions. If the dew point is high, the splitting of the capsules is accelerated as each opening appears to increase the rupturing along the suture between the carpels. When the dew point is low, there is less splitting of the capsule. A capsule may show a different rate of capsule split on each side of the capsule, and in this case, the greater split measurement is taken.

A desirable phenotypic character utilized in the breeding of non-dehiscent sesame plants is capsule split for both sides from the top of the capsule to approximately the base of the capsule, or TS1 (FIG. 2a). This rupturing of the epidermis and mesocarp is critical in making it easier to thresh the capsule in the combine. In lines where the split is not complete, the threshing must be more aggressive to remove the seed from the capsule. This additional aggressiveness can break the seed.

Capsule Opening ("TO")

Figure 3A:
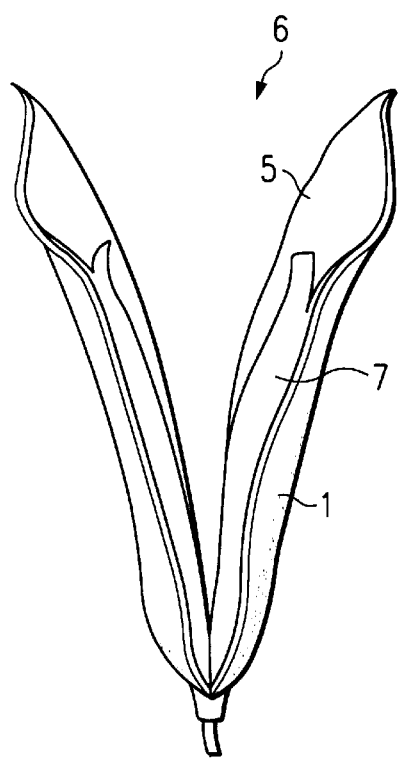
FIG. 3A–FIG. 3C depict capsule opening (TO), characterized by splitting of the carpel (1) and membrane (7) at the suture exposing the seeds (not shown) and/or seed chamber (5). The drawings show a scale for measuring capsule opening wherein TO0 represents capsule opening to the bottom of the seed chamber, TO8 represents capsule opening at the top of the seed chamber, and TO4 represents capsule opening to the middle of the seed chamber. For clarification, the figures show the capsule without seeds.
Figure 3B:
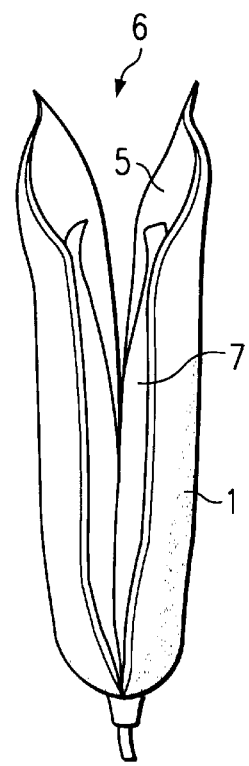
Figure 3C:
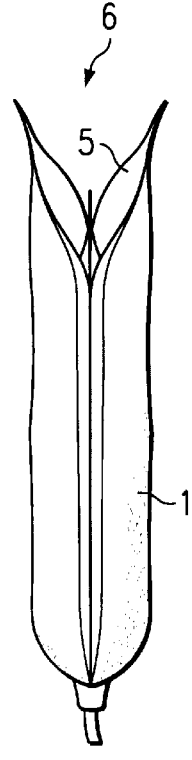

Another character found to be important in selection of candidate plants for breeding is capsule opening. As the capsule splits the epidermis and mesocarp layers of cells along the suture, the carpels can open between the membranes, exposing the seed. The level of opening between these membranes is shown in FIG. 3A–3C. It is desirable to select candidate breeding plants with a TO character between TO6 and TO7 according to the scale set forth in Table I. TO6 and TO7 are defined as slightly open to barely open, respectively. It is desirable for the non-dehiscent lines to exhibit an opening at the top of the membrane, ranging from moderate to barely open, which generally reveals only the top two to three seeds in each locule. The capsule opening acts as a vent for moisture and to allow a starting point for the combine to open the capsule for release of the seed. At plant physiological maturity, the capsules in the center of the capsule zone have approximately 51–60% moisture which must be reduced substantially before harvest. Without an opening, moisture has to escape by migrating through the capsule wall. With an opening, the moisture can escape through the tip. The advantage of capsules with an opening can be seen in that a field of indehiscent or seamless sesame ready for harvest cannot be harvested until five to seven days after a light rain, whereas a field of sesame with an opening in the capsule can be harvested within one to two days following a light rain, allowing for less exposure to adverse weather conditions. Further, while indehiscent or seamless lines require that the capsule be broken across the locule for the seed to be released, having a capsule opening allows the seed to escape from the capsule without first breaking the capsule, thus assisting in mechanized harvesting. There are indehiscent and seamless lines with a slight opening at the top. However, the indehiscent and seamless lines do not have the TS to the base of the capsule and thus do not open as readily in the combine.

Capsule Membrane Completeness ("TM")

Another character to be evaluated in candidate plants to be used in the method of the invention is capsule membrane completeness. In some known lines of sesame, there are no membranes between the carpels, and the absence of membranes allows seed to fall out when the capsule opens. In some lines, portions of the membrane are missing as shown in FIGS. 4A–4B. Capsule membrane completeness is preferably TM7, or complete membrane, in non-dehiscent lines. All known lines of sesame have an opening in the top of the membrane which allows the seed to slip out of the capsule. This hole must be present or the threshing will have to be too aggressive. With the exception of membraneless lines, the parts of the membrane missing varies from capsule to capsule within the plant. This rating is based on opening ten capsules and averaging the missing membranes.

Capsule Constriction ("TC")

Figure 7A:
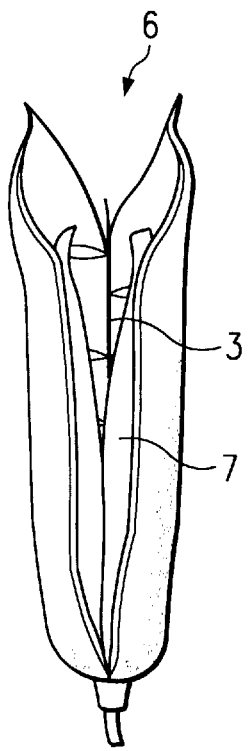
FIG. 7A–FIG. 7D depict capsule placenta attachment (TP), characterized by the degree to which the seeds (9) are attached to the capsule placenta (3). Capsule placenta attachment is scaled as TP0 representing no capsule placenta attachment, TP8 representing full capsule placenta attachment, and TP4 representing moderate capsule placenta attachment.
Figure 7B:
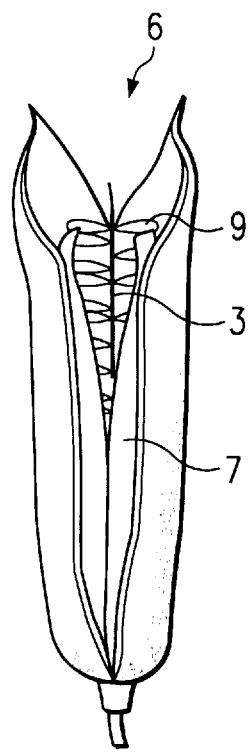
Figure 7C:
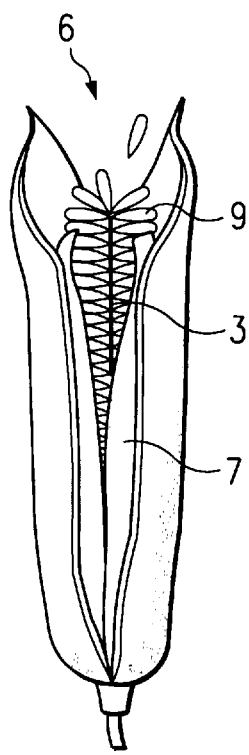
Figure 7D:
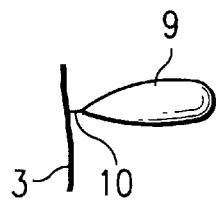
Figure 8A:
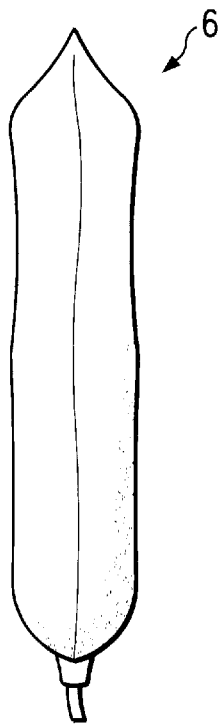
FIG. 8A–FIG. 8B depict an indehiscent capsule.
Figure 8B:
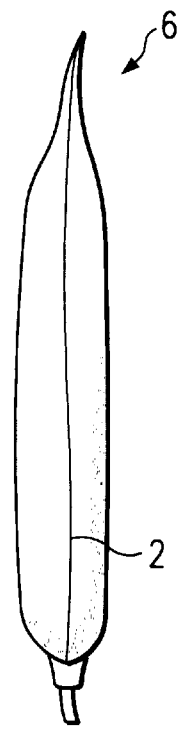
Figure 9A:
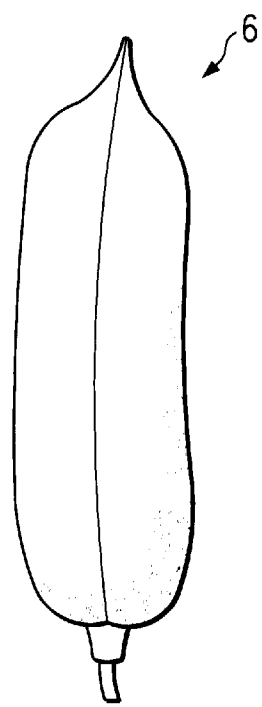
FIGS. 9A and 9B depict a seamless capsule.
Figure 9B:

Another character to be evaluated in candidate plants to be used in the method of the invention is capsule constriction. The degree of constriction of the capsule around the seeds prevents seed from falling out of the capsule through the capsule opening. This characteristic is measured as capsule constriction. When the carpels are separated, the placenta (the part of the capsule the seeds are attached to through placenta attachment as shown in FIG. 7D) will go with one carpel or the other. Constriction can be determined in the carpel without the placenta and thus independent of placenta attachment. This carpel can be inverted and the amount of seed remaining in the capsule determines the amount of constriction as shown in FIGS. 5A–5C. The desirable range for capsule constriction is TC3 to TC5, or moderate seed retention. Ratings of TC6 to TC8 make it difficult to get the seed out of the capsule in the combine. Ratings of TC0 to TC2 are associated with capsules that allow the seed to rattle in the base and apply pressure to the upper seed, thus breaking the placenta attachment.

Capsule Membrane Attachment ("TA")

Figure 6A:
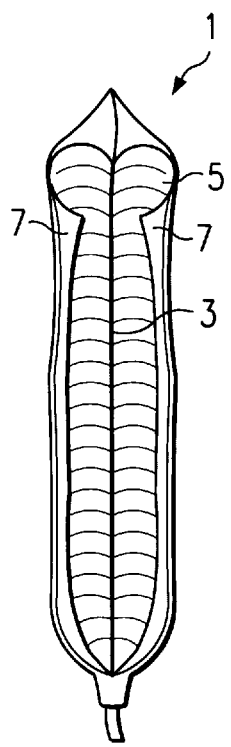
FIG. 6A–FIG. 6C depict capsule membrane attachment (TA), characterized by the amount of separation between the membrane (7) and placenta (3). Capsule membrane attachment is scaled as TA0 representing no membrane, TA8 representing no separation, and TA4 representing medium separation between the membrane and placenta. For clarification, the figures show the capsules without seeds.
Figure 6B:
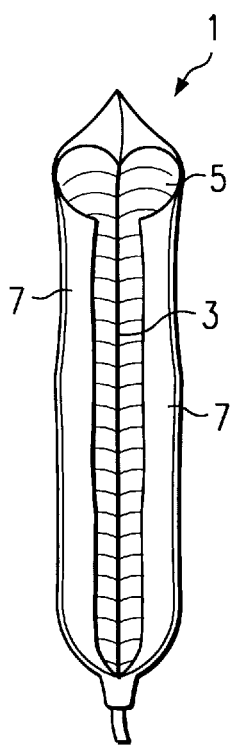
Figure 6C:
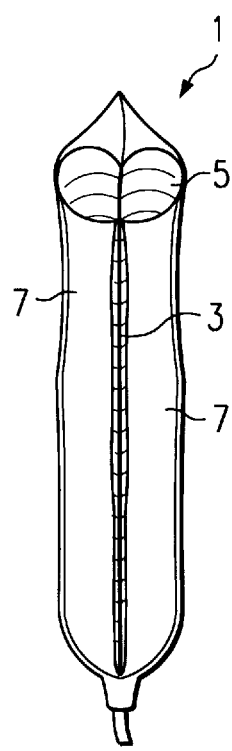

Another character to be evaluated in candidate plants to be used in the method of the invention is capsule membrane attachment. This is a characteristic having a high correlation with non-dehiscent lines. When the capsule is opened, most non-dehiscent lines have a membrane that extends adjacent to the placenta. By adjacent, it is meant that a rating of moderate to little separation between the membrane and placenta is observable. More specifically, when the carpels in a capsule are separated, the edges of the membrane can pull away from the placenta. The rating is, therefore, taken by restoring the membrane to its natural position as shown in FIGS. 6A–6C, so that any folds, curls, or distortions of the membrane caused by opening the capsule are eliminated prior to taking the rating. Non-dehiscent lines have preferred ratings of TA5 to TA8, or moderate to little separation between the membrane and placenta.

Placenta Attachment ("TP")

Another character to be evaluated in candidate plants to be used in the method of the invention is attachment of the seed to the placenta through a placenta attachment. During growth, all sesame seeds are attached to the placenta through a placenta attachment. At physiological maturity of the seed, the placenta attachment will dry. There are lines where the dry placenta attachment will keep the seed attached to the placenta, and other lines, where the placenta attachment breaks under normal drydown conditions as shown in FIGS. 7A–7C. The level of placenta attachment is the most critical aspect of non-dehiscent sesame. The TP rating needs to be between TP6 and TP8, or moderate to good capsule placenta attachment at the top of the capsule, but the higher the rating, the better. When most capsules first open, the rating is often TP7 to TP8, but within a few days with even slight breezes and rubbing of capsules against neighboring plants or other capsules, on most lines, the placenta attachment breaks down and the seeds begin to fall out of the capsules. Unlike the placenta attachment described by Yermanos as weakened and obliterated in dry capsules, the preferred placenta attachment does not weaken on dry down. The ideal placenta attachment is one that will hold the seed in the capsules even for an extended period during bad weather in terms of wind and moisture (dews or rain). However, the placenta attachment must be weak enough to release the seed once the capsule is inside the combine. To date, no lines with too much placenta attachment to prevent release of the seed within the combine are known.

In some lines, there is a difference in the amount of placenta attachment within the capsule. Good placenta attachment at the base of the capsule is not essential when there is good attachment at the top of the capsule. The seed held at the top blocks the bottom seed from exiting the capsule.

Interrelationships between Capsule Characters

On all six characters, better ratings of one can offset lower ratings on other characters. There is a small allowance between lines that hold enough and lines that hold too much. The plants must hold the seeds until in the combine but must release the seeds within the combine as easily as possible with as little breakage of seeds as possible.

TS and TO

It has been found that with high TS ratings, the capsules do not open readily in the combine, requiring more aggressive threshing. The adhesion between the membranes is essential. Non-dehiscent sesame needs high TO ratings and low TS ratings.

TO and TM

Generally, there is a correlation between TM and TO in that if there are parts of the membranes missing, there is less adhesion between the carpels, and the TO rating will be low. Thus, although high TM ratings do not necessarily lead to high TO ratings, low TM ratings are usually associated with low TO ratings.

TO and TP

A high TP rating can offset a lower TO rating. However, a high TO rating will not offset a lower TP rating.

TO and TA

The added membrane surface on a high TA rating provides more adhesion between the membranes. This allows the capsule to split at the epidermis and mesocarp but not open to expose the seed. Thus, although high TA ratings do not necessarily lead to high TO ratings, low TA ratings are usually associated with low TO ratings.

TC and TA

A higher TA rating is usually associated with a high TC rating. The space between the membrane and placenta should be just large enough to provide sufficient volume around the seeds to reduce constriction. When TA=8, there is too much constriction.

TC and TP

Higher TC ratings can offset lower TP ratings. There are lines that hold enough seed to qualify as non-dehiscent through TC alone, but these lines do not release the seed in the combine. Logically, if the TP is high enough, and in combination with TO, the top of the capsule is blocked from releasing seed, no constriction would be necessary. However, to date, all non-dehiscent lines have some constriction.

Methodology for Developing Non-Dehiscent Sesame

By incorporating the above-identified shatter resistant characters into commercially suitable sesame lines, non-dehiscent sesame lines have been developed. The starting point for developing non-dehiscent sesame is acquisition of lines which have the shatter resistant characters. Representative sources for sesame lines necessary for the development of non-dehiscent sesame lines include the National Seed Storage Laboratory (NSSL) in Ft. Collins, Colo., and the Plant Genetic Resources Conservation Unit (S9) in Griffin, Ga. These collections were also deposited with the Food and Agriculture Organization of the United Nations (FAO) sesame collections maintained in South Korea and Kenya. In order to ensure the purity of these lines, one can grow out the materials for a year before selecting initial parent plants with required capsule characters. Table II provides representative sources for the different capsule characters required for developing non-dehiscent sesame, and reference to specific lines and crosses in the following discussion are made by SID codes.

The line 111 has the best TO, but it is offset by not having enough TS. The TO in 118, 700, 701, and 702 is not good enough for non-dehiscence, but crosses between these four lines and 111 are the fastest avenue to the preferred amount of TS and TO. The line 111 has too much TC, while 118, 700, 701, and 702 do not have enough TC. Crosses between these four lines and 111 are the fastest avenue to the preferred amount of TC. Crosses between 118, 700, 701, and 702 and 111 also provide the preferred level of TA and TM.

TABLE II

Sources for Capsule Characters Used in Development of Non-dehiscent Sesame

| Character | SID[a] | SESAN[b] | Sesame PI Number[c] |
|---|---|---|---|
| Capsule split (TS) | 118 | T118 | PI 426944 |
| | 700 | T700 | PI 292144 |
| | 701 | T701 | PI 292145 |

TABLE II-continued

Sources for Capsule Characters Used in Development of Non-dehiscent Sesame

| Character | SID[a] | SESAN[b] | Sesame PI Number[c] |
|---|---|---|---|
| | 702 | T702 | PI 292146 |
| Capsule opening (TO) | 118 | T118 | PI 426944 |
| | 111 | T111 | PI 173955 |
| | 700 | T700 | PI 292144 |
| | 701 | T701 | PI 292145 |
| | 702 | T702 | PI 292146 |
| Capsule membrane completeness (TM) | 118 | T118 | PI 426944 |
| | 111 | T111 | PI 173955 |
| | 700 | T700 | PI 292144 |
| | 701 | T701 | PI 292145 |
| | 702 | T702 | PI 292146 |
| Capsule constriction (TC) | 111 | T111 | PI 173955 |
| Capsule membrane attachment (TA) | 700 | T700 | PI 292144 |
| | 701 | T701 | PI 292145 |
| | 702 | T702 | PI 292146 |
| Placenta attachment (TP) | ACE | TACE | PI 320959 |
| | 191 | T191 | d |
| | 192 | T192 | d |
| | 193 | T193 | d |

[a]Significant lines were given three character sesame identifiers (SID).
[b]When lines were aquired from the NSSL and S9 collections, PI numbers were converted to Sesanumbers (SESAN).
[c]NSSL and S9 identifying codes.

The capsule architecture in terms of length and width of the above-identified five lines is similar in size enough to allow for quick selection of a line with the proper amount of TS, TO, TM, TC, and TA. In making these selections, leaving the plants in the weather for at least a month after drydown is essential, since the TO can break down over time and thus prevent accurate measurement of weather resistant TO. When looking at the 118, 700, 701, and 702 capsules at drydown, it might appear that the crosses with 111 are not necessary, but they are essential, since 111 either provides the correct amount of adhesion or a reduction in the layers of the mesocarp that allows less opening force.

Having strong enough TP is essential in developing non-dehiscence. The lines 111, 118, 700, 701, and 702 lines do not have sufficient TP to provide non-dehiscence. Therefore, preferably crosses are made between these lines and lines which have strong TP, e.g., both the 191/192/193 (representing herein "191, 192, or 193") U.S. lines and the ACE Venezuelan line (equivalent to G8 in FIG. 10, FIG. 11, and FIG. 12). Less preferred is a method crossing with just one of the groups 191/192/193 or ACE. Preferably, the 191/192/193 group is utilized.

In terms of the importance of the characters, the placenta attachment (TP) and capsule opening (TO) are the two most important characters for seed retention, and the capsule split (TS) and capsule constriction (TC) are the most important characters for seed release in the combine.

Crossing of sesame may be done using standard techniques as generally outlined below. Sesame is generally self-pollinated. Flowers develop and mature from the base of the plant to the top. Each morning, flowers open, and shortly before or after opening, the anthers burst longitudinally, releasing the pollen. Simultaneously, the lobes of the stigma open and receive large quantities of pollen. In order to cross sesame, the flowers must be emasculated prior to pollination. Most sesame flowers have a fused corolla with the stamens attached to the corolla. The evening before the flowers are to open, the corolla (with stamens) is removed from the female flower. Similarly, the corolla is removed from the male flower and stored in a container overnight. The next morning, the pollen from the male flower is put onto the stigma of the female flower. There are many variations in specific techniques as detailed in Langham, D. G. 1944. "Natural and controlled pollination in sesame," *J Heredity* 35:254–256; Yermanos, D. M. 1980. "Sesame. Hybridization of crop plants," *Am Soc Agronomy-Crop Sci of America*, pp. 549–563; and Osman, H. E. 1985. "Studies in sesame: Hybridization and related techniques," *FAO Plant Production and Protection Paper No. 66*, pg. 145–156. Each cross provides 40 to 80 seeds and usually a minimum of two flowers are available to cross each day. The F1 plants can be grown in a greenhouse since selection for capsule characters needs to be done in the F2 plants and not the F1 plants. The greenhouse does not provide an adequate environment to select for preferred capsule characters in any generation beyond F1, since wind is not a factor and there is not enough variability in moisture in terms of humidity, rain, fog, and dew in a greenhouse.

Preferably, the shatter resistant characters are aggregated into one line and then this line is crossed against commercially suitable sesame lines. In crossing non-dehiscent sesame lines against commercially acceptable shattering lines, there is no shatter resistance in the F1 plants. In most crosses, there will be individual F2 plants with enough shatter resistance to be tested for non-dehiscence. The larger the F2 population, the greater the chance of finding non-dehiscent F2 plants.

Under ideal conditions, in Year 1, crosses between 111 and 118/700/701/702 (representing herein "118, 700, 701, or 702") are made in a greenhouse/winter nursery to the F1 plants, grown in a greenhouse/winter nursery; and the F2 plants, grown in the field. The F2 plants are examined to find one or more plants having appropriate TS, TO, TM, TC, and TA characters, providing Stage 1 selections. In Year 2, Stage 1 selections are crossed with ACE/191/192/193 in a greenhouse/winter nursery; the F1 plants, grown in a greenhouse/winter nursery; and the F2 plants, grown in the field. The F2 plants are examined to find one or more plants having appropriate TS, TO, TM, TC, TA, and TP characters, providing Stage 2 selections. By the end of Year 2, at least one of the Stage 2 selections is non-dehiscent. Although it is possible to find F2 plants with non-dehiscence, most non-dehiscent F2 and F3 plants segregate lower levels of shatter resistance, and most pure non-dehiscent lines have been selected at the F4 level. Moreover, if the plants for making the initial crosses are obtained in the spring, an additional half year is necessary, since it is essential that the F2 plants are grown in the field so that non-dehiscence is measurable upon exposure to adverse weather conditions.

In order to increase the odds of success, all permutations are crossed except the intercrossing within the following two groups: 118/700/701/702 and 191/192/193. Each line is used as both male and female. In other words, the following crosses are made:

111×118, 111×700, 111×701, 111×702, 111×ACE, 111×191, 111×192, 111×193,

118×ACE, 118×191, 118×192, 118×193,

700×ACE, 700×191, 700×192, 700×193,

701×ACE, 701×191, 701×192, 701×193,

702×ACE, 702×191, 702×192, 702×193,

ACE×191, ACE×192, and ACE×193.

The reciprocal crosses should also be made, i.e., 118×111, 700×111, 702×111, etc. This is a total of 54 crosses. Doubling the crosses using different parent plants improves the odds of success.

Selections of the F2 plants having the preferred combination of shatter resistant characters are made, and then a crossing plan is designed based on the combinations found in the F2 plants. Again, a large number of crosses (about 100–250 crosses) are made to increase the odds of success in producing the proper combination of genes. Preferably, crosses of ACE, 191, 192, and 193 against the F1 plants of 111×118 700 701 702 ACE 191 192 193 are made to provide the potential of an earlier F2 population that would have the appropriate mixture of shatter resistant characters. However, large populations (about 5,000–30,000 plants) of the latter scheme must be grown out.

The genetic controls for the shatter resistant characters have not yet been determined. However, given the percentage of F2 plants that segregate with the proper combinations of characters, more than one gene is involved in each character. While there are no genetic maps of sesame, the fact that all of the shatter resistant characters have been moved together in many different paths indicates that none of the genes are on chromosomes in such a way that cross overs are necessary for success. Although the genes responsible for non-dehiscence have not yet been established, it is believed that once these genes are isolated, it will be possible to inject these genes into cells or protoplasts taken from sesame plants lacking non-dehiscence, thus producing from these injected cells or protoplasts plants which exhibit non-dehiscence.

Crosses between non-dehiscent lines and other commercially suitable lines are providing selectable non-dehiscence in the F2 plants. In some cases, the F2 selections are pure for non-dehiscence. Thus, the preferred method of producing commercially acceptable, non-dehiscent sesame is to make non-dehiscence the first criteria for selection and then move non-dehiscence to commercially suitable lines.

The present invention relates to non-dehiscent sesame seed and the sesame plant produced therefrom. It also relates to seeds and plants produced by crossing each non-dehiscent variety with itself, another non-dehiscent variety, or other sesame varieties. Sesame lines S22, S23, S24, 19A, and 11W (representative seed having been deposited under ATCC accession number PTA-1400, PTA-1401, PTA-1402, PTA-1398, and PTA-1399, respectively) are exemplary non-dehiscent sesame lines which have been found to be readily reproducible over successive planting seasons. Unless otherwise stated, as used herein, the term plant includes plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like. Further, unless otherwise stated, as used herein, the term progeny includes plants derived from plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like.

Tissue culture of sesame is currently being practiced in Korea, Japan, Sri Lanka and United States. It is possible for one of ordinary skill in the art to utilize sesame plants grown from tissue culture as parental lines in the production of non-dehiscent sesame. Further, it is possible to propagate non-dehiscent sesame through tissue culture methods.

EXAMPLE 1

Breeding Program for Non-Dehiscent Sesame

Figure 11:
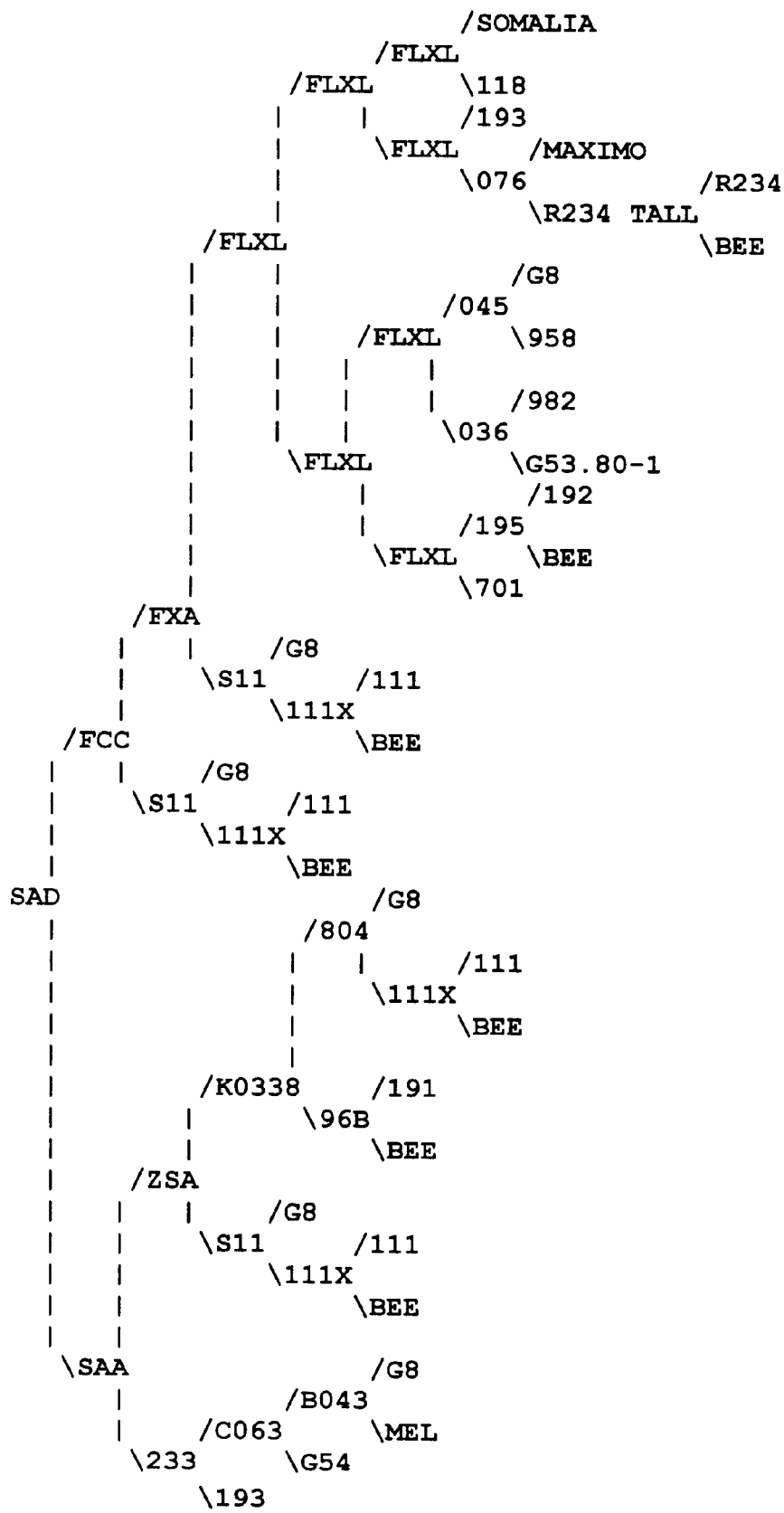
FIG. 11 is a crossing schematic for the SAD non-dehiscent sesame plant.

Non-dehiscent sesame was developed by crossing lines with various shatter resistant characteristics. Over thirtyseven lines have been developed and tested. FIGS. 10–12 demonstrate three different avenues by which non-dehiscent lines were developed. In reading the diagrams from right to left, the initial SIDs can be seen.

The sources in Table II are not non-dehiscent, and also not suitable to be used as commercial varieties in the United States. These sources were crossed against lines having commercially preferred characters such as light color and disease resistance. Commercially acceptable, non-dehiscent lines were obtained. It was determined that with the exception of G8 (a sister selection of ACE), none of the lines in FIG. 10–FIG. 12 not listed in Table II contributed to non-dehiscent capsules.

Methodology for Measuring Non-dehiscence

Non-dehiscent sesame are characterized by sufficient retention of seed within the capsules while in the field and ready release of the seed from the capsules during mechanized harvesting with minimal breakage of the seed. Methods for measuring the retention of seed in capsule in the field, release of seed from the capsule during harvest, and breakage of seed during harvest have been developed.

Subjective Shatter Resistance Screening Measurement

The crossing methodology described above results in thousands of segregating plants, and an initial screening method has been developed for selecting plants to be submitted for a more stringent, objective measurement of shatter resistance as an indicator of non-dehiscence. This screening method for measuring shatter resistance is a rating system based on the two parameters outlined in Table III below. Based on Table III, FIGS. 5A–5C illustrate the amount of seed present in the dry capsules for TI and KE. FIG. 5A represents TI1 and KE1; FIG. 5B represents TI4 and KE4; and FIG. 5C represents TI7 and KE7.

TABLE III

Parameters Used in Rating Shatter Resistance

| Name/ Abbreviation | Measurement | Rating/value System |
|---|---|---|
| Upright seed retention (TI) | amount of seed present in the dry capsule with the capsule still remaining on the plant, measured by how close the seed is to the tip of the capsule | scale of 0–8; 1 = at the bottom of the capsule, 4 = halfway up the capsule; 7 = at the tip of the capsule; 8 = indehiscent or seamless capsule |
| Inverted seed retention (KE) | amount of seed present scale of 0–8; capsule after the capsule is gently removed from the plant, inverted, and twirled | scale of 0–8; 1 = at the bottom of the capsule, 4 = halfway up the capsule; 7 = at the tip of the capsule; 8 = indehiscent or seamless capsule |

The TI and KE parameters have been combined into a two digit hold (HLD) rating. By this method of shatter resistance measurement, non-dehiscence is preferably defined by a hold rating with TI6–TI7 and KE6–KE7, i.e., HLD=66 or above. Hold ratings may deteriorate through various stages: first stage=when plant is first dry; second stage=fourteen days after drydown with no adverse weather conditions such as wind and/or rain; third stage=one week after exposure to adverse conditions; and fourth stage=one month after drydown and exposure to adverse weather conditions. Non-dehiscent sesame demonstrates a HLD rating of 66 or above at all four stages. This screening method is limited in that while it estimates the amount seed retention (TI) and seed release (KE), it does not provide an objective measurement of the amount of seed release and seed breakage during mechanized harvesting.

Objective Shatter Resistance Measurement

Since all of the capsule character ratings presented herein are subjective and can be dependent on the time of observation in relation to complete drydown, shatter resistance cannot be objectively measured directly from capsule character ratings. Since the screening method described above provides only a subjective measurement of shatter resistance, objective methodologies have been developed.
Seed Retention Examples 2 and 3 give methods for determining the first requirement of non-dehiscence, i.e., retention of seeds in the capsule.

EXAMPLE 2

Seed Retention Measurement by Natural Means

One method for measuring shatter resistance to determine non-dehiscence involves evaluating retention of seed in capsules before and after exposure to adverse weather conditions. Testing fields should be located where the sesame will be subject to wind and rain after drydown.

Initially, representative lots of ten capsules were removed from different lines in a sesame nursery during a normal harvest at initial drydown while the capsules were still holding all of their seeds, i.e., HLD=77. The weight of the seeds in each lot established an average baseline weight of seeds per ten capsules. Three months after initial drydown and exposure to inclement weather, a second representative lot of ten capsules was taken from the same plot. The average weight of seed retained in ten capsules in the second round was divided by the average baseline weight from the first round to determine the percentage of retention, providing a measurement of weather shatter resistance.

By this method of measuring shatter resistance, non-dehiscent lines have from about 65% to about 97% retention of seed after exposure to adverse weather conditions. While this method has the disadvantage of leaving the sesame in the field for extended periods after drydown, it can be used in remote areas where more technical methods are not possible.

EXAMPLE 3

Mechanized Seed Retention Measurement

While the weather shatter resistance method in Example 2 is one method for measuring shatter resistance to determine non-dehiscence, it is generally not practical to leave a sesame nursery for over three months past harvest to measure seed retention. Consequently, a methodology using a machine has been developed to simulate the weathering of capsules.

After examining the shaking action of several machines, a reciprocal shaker was chosen to simulate weather conditions in the determination of sesame seed retention rates.

Some of the capsules at initial drydown were used to calibrate the shaker. A Lab-line Reciprocal Shaker (Lab-line Instruments, Inc., Melrose Park, Ill.) was set at a stroke length of 1.5 inches and 250 strokes per minute. Ten capsules were placed into a 250 ml Erlenmeyer flask and shaken for five minutes, and loose seed was removed and weighed. The capsules were shaken for an additional five minutes, and the loose seed was removed and weighed. The capsules were shaken for an additional five minutes, and the loose seed was removed and weighed. The seed retained in the capsules was removed and weighed.

The weights from the shaker test were then compared to weights obtained by the weathering procedure given in Example 2. It was determined that there were differences between the shaker retention rate and the natural weathering retention rate in the 5, 10, and 15 minute tests, but that ten minutes was the best fit with the lowest differences between the shaker shatter resistance and the weather shatter resistance. Retention rates of samples shaken for 5 minutes were higher than the retention rate of the weathered samples. Retention rates of samples shaken for 15 minutes were lower than the retention rates of the weathered samples. Some samples shaken for 10 minutes had lower retention rates than those for weather samples, and other samples shaken for 10 minutes had higher retention rates than those for weather samples. Retention rates for samples shaken for ten straight minutes were compared to retention rates for samples shaken for two five-minute increments. There were no significant differences between the two groups.

The preferred method for measuring seed retention in sesame as a measurement of non-dehiscence is summarized as follows. Ten capsules from the center of the capsule zone are harvested when the plants have 90–95% dry capsules, typically within about two weeks of initial drydown. Only capsules with all their seed are chosen. Only lines that have 95% of their capsules holding all the seed should be tested. If the plot is segregating hold, it should not be a candidate for non-dehiscent testing. On lines having a single capsule per leaf axil, two capsules are taken from five plants in the middle of the capsule zone. On lines having triple capsules per leaf axil, two capsules from the same leaf axil are taken from five plants. The plants should be in normal populations in the center of the rows or more than half a meter from end plants or plants at the edge of a gap, and should not be from a row on the edge of a planting block. The capsules are then dried down using heat lamps or ovens. The capsules are placed in a 250 ml Erlenmeyer flask and submitted to the shaker test, with a Lab-line reciprocal shaker preferably at a stroke length of 1.5 inches and run at 250 strokes per minute for 10 minutes. The seed released from the capsules is removed from the flask and weighed. The seed retained in the capsules is threshed, removed from the flask, and weighed. Shaker shatter resistance (SSR) equals the weight of the retained seed divided by the sum of the released and retained seed multiplied by 100 equals the percent seed retention. The procedure should be repeated a minimum of four more times. Statistically, the lowest and highest SSR should be discarded and the other values averaged to determine the line SSR. Non-dehiscent, indehiscent, and seamless sesame retain about 65% or more of the seed by this method.

Other types of shakers may be used to perform the shaker test. However, the stroke length, shaking speed, and shaking time must be calibrated for each type of shaker to determine the parameters which correlate to the retention rate of weathered samples.

While seed retention can be measured by the weathering method of Example 2 or the shaker method of Example 3, the shaker method has significant advantages over the weathering method. The shaker method provides quicker results since the sesame does not have to be exposed to extended weathering periods. The weathering method may give inconsistent results from one crop to another since weather patterns will vary from one season to another and from one location to another. In contrast, the shaker method is not weather dependent and provides more consistent results.

Seed Release/Breakage During Mechanized Harvesting: Thresh Yield Tests

To test for the second requirement of non-dehiscent sesame, i.e., high yield during mechanized harvesting, Examples 4 and 5 provide methods by which seed release and seed release/breakage, respectively, are determined.

EXAMPLE 4

Plot Thresher Screening Method

Plot threshers can be used to screen for capsule seed retention vs. seed yield rates. Capsules taken from the plot thresher are opened and examined for seed retention. The capsules from non-dehiscent lines have about 90% of the seed removed from the capsule by the thresher, while homozygous indehiscent lines, homozygous seamless lines, and lines with high TS and/or high TC retain more than 10% of the seed in the capsules. While plot threshers provide an indication of the seed yield rate, they do not provide a measurement of seed breakage during mechanized harvesting. The plot threshers are, thus, used to identify crops which are to be subjected to the more definitive combine test.

EXAMPLE 5

Combine Method for Measuring Seed Yield

The preferred method for the thresh yield test measures the amount of seed released and the amount of seed broken during harvesting in a combine. A sesame crop of not less than ten acres having a seed moisture content of about 6% or less is selected for combining. The combine is set for the field conditions such that the seed is threshed as gently as possible. Generally, this means a low cylinder speed and wide open concaves. For example, a John Deere 9600 combine is adjusted to the lowest cylinder speed with the concave adjusted to the "corn" setting and air at the minimum setting; and while threshing, the concave is adjusted toward the "soy" setting until mature seeds are removed from the capsules. On an IHC 1680 combine, initial settings are cylinder 350, air 450, and fine grain concave with wires in. Most sesame will have capsules at the top of the plant that do not contain mature seed, and this immature seed is not counted in these tests. Once the combine is set to obtain 99%–100% release of seed with broken seeds at less than or equal to 2%, the seed gathered during the setting process is dumped.

To get a representative sample, the combining test is begun and continues until the bin is full up to the input auger. With a four foot probe, samples are taken from four locations in the combine bin, and the samples are co-mingled. While the combine is operating, at a minimum of 100 feet from the end of the field, five capsules are taken from each of twenty plants at positions ranging from the bottom to the top of the plant but not including the immature seed capsules at the very top. In the same area, a container such as an oil changing pan is thrown between the wheels of the combine as it passes to catch the capsules that have gone through the combine and are going over the top of the screens/sieves.

This procedure is repeated four more times. In the laboratory, the seed is threshed out of the 100 capsules taken from the twenty plants, and the seed is weighed. At random, 100 representative capsules that came out of the combine are selected. Seed from these capsules are threshed out and weighed. The weight of seed retained in the capsules is divided by the weight of the 100 capsules taken prior to combining. The seed samples taken from the combine bin are thoroughly mixed and a 60 gram sample is taken. The seeds are separated into three groups: whole sesame seeds, broken seeds, and non-sesame chaff/foreign matter/immature seeds. After weighing the first two groups, the weight of the broken seeds is divided by the sum of the weights of the whole seeds and the broken seeds.

In non-dehiscent lines, the capsules preferably retain less than or equal to about 10% of the seed during combining. Comparatively, indehiscent and seamless lines retain more than 10% of the seed during combining. More preferably, non-dehiscent lines have less than about 7% broken seeds by weight after combining, whereas indehiscent and seamless lines have more than 7% broken seeds. Thus, non-dehiscent lines are identified as having about 65% or more seed retention using the mechanical shaker test, about 10% or less seed retention in the thresh yield test, and less than or equal to about 7% broken seed in the thresh yield test.

I claim:

1. A non-dehiscent sesame plant characterized by having greater than or equal to about 65% of total amount of sesame seed in each capsule retained in unharvested capsules subjected to the shaker test, less than or equal to 10% of total amount of sesame seed in each capsule retained in capsules after mechanical harvesting, and less than or equal to about 3% of total amount of sesame seed which is released from capsules broken during mechanical harvest.

2. A progeny plant from a non-dehiscent sesame parent plant, said parent plant characterized by having greater than or equal to about 65% of total amount of sesame seed in each capsule retained in unharvested capsules subjected to the shaker test, less than or equal to 10% of total amount of sesame seed in each capsule retained in capsules after mechanical harvesting, and less than or equal to about 3% of total amount of sesame seed which is released from capsules broken during mechanical harvest, wherein said progeny plant possesses non-dehiscence derived from said parent plant.

3. Seeds produced by a non-dehiscent sesame plant, said non-dehiscent sesame plant characterized by having greater than or equal to about 65% of total amount of sesame seed in each capsule retained in unharvested capsules subjected to the shaker test, less than or equal to 10% of total amount of sesame seed in each capsule retained in capsules after mechanical harvesting, and less than or equal to about 3% of total amount of sesame seed which is released from capsules broken during mechanical harvest.

4. A progeny plant from seeds produced by a non-dehiscent sesame parent plant, said parent plant characterized by having greater than or equal to about 65% of total amount of sesame seed in each capsule retained in unharvested capsules subjected to the shaker test, less than or equal to 10% of total amount of sesame seed in each capsule retained in capsules after mechanical harvesting, and less than or equal to about 3% of total amount of sesame seed which is released from capsules broken during mechanical harvest, wherein said progeny plant possesses non-dehiscence derived from said parent plant.

5. A non-dehiscent sesame plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 7% of total amount of sesame seed which is released from capsules broken during mechanical harvesting.

6. A progeny plant from a non-dehiscent sesame parent plant, said parent plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 7% of total amount of sesame seed which is released from capsules broken during mechanical harvesting, wherein said progeny plant possesses non-dehiscence derived from said parent plant.

7. Seeds produced by a non-dehiscent sesame plant, said non-dehiscent sesame plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 7% of total amount of sesame seed which is released from capsules broken during mechanical harvesting.

8. A progeny plant from seeds produced by a non-dehiscent sesame parent plant, said parent plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 7% of total amount of sesame seed which is released from capsules broken during mechanical harvesting, wherein said progeny plant possesses non-dehiscence derived from said parent plant.

9. A non-dehiscent sesame plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 3% of total amount of sesame seed which is released from capsules broken during mechanical harvesting.

10. A progeny plant from a non-dehiscent sesame parent plant, said parent plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 3% of total amount of sesame seed which is released from capsules broken during mechanical harvesting, wherein said progeny plant possesses non-dehiscence derived from said parent plant.

11. Seeds produced by a non-dehiscent sesame plant, said non-dehiscent sesame plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 3% of total amount of sesame seed which is released from capsules broken during mechanical harvesting.

12. A progeny plant from seeds produced by a non-dehiscent sesame parent plant characterized by having greater than or equal to about 65% of total amount of sesame seed in each capsule retained in unharvested capsules subjected to the shaker test, less than or equal to 5% of total amount of sesame seed in each capsule retained in capsules after mechanical harvesting, and less than or equal to about 3% of total amount of sesame seed which is released from capsules broken during mechanical harvesting, wherein said progeny plant possesses non-dehiscence derived from said parent plant.

13. A non-dehiscent sesame plant which produces a capsule having a placenta, a membrane, and seed, said capsule characterized by a capsule opening of slightly to barely open and moderate to good capsule placenta attachment.

14. The plant of claim 13, wherein said capsule is further characterized by moderate capsule constriction.

15. The plant of claim 13, wherein said capsule is further characterized by a complete capsule membrane.

16. The plant of claim 14, wherein said capsule is further characterized by a complete capsule membrane.

17. The plant of claim 13, wherein said capsule is further characterized by having a capsule split, said split extending from the top of the capsule to approximately the base of the capsule.

18. The plant of claim 14, wherein said capsule is further characterized by having a capsule split, said split extending from the top of the capsule to approximately the base of the capsule.

19. The plant of claim 15, wherein said capsule is further characterized by having a capsule split, said split extending from the top of the capsule to approximately the base of the capsule.

20. The plant of claim 16, wherein said capsule is further characterized by having a capsule split, said split extending from the top of the capsule to approximately the base of the capsule.

21. The plant of claim 13, wherein said membrane is situated adjacent to said placenta, and wherein a capsule membrane attachment rating of moderate to little separation between the membrane and placenta is observable.

22. The plant of claim 14, wherein said membrane is situated adjacent to said placenta, and wherein a capsule membrane attachment rating of moderate to little separation between the membrane and placenta is observable.

23. The plant of claim 15, wherein said membrane is situated adjacent to said placenta, and wherein a capsule membrane attachment rating of moderate to little separation between the membrane and placenta is observable.

24. The plant of claim 16, wherein said membrane is situated adjacent to said placenta, and wherein a capsule membrane attachment rating of moderate to little separation between the membrane and placenta is observable.

25. The plant of claim 17, wherein said membrane is situated adjacent to said placenta, and wherein a capsule membrane attachment rating of moderate to little separation between the membrane and placenta is observable.

26. The plant of claim 18, wherein said membrane is situated adjacent to said placenta, and wherein a capsule membrane attachment rating of moderate to little separation between the membrane and placenta is observable.

27. The plant of claim 19, wherein said membrane is situated adjacent to said placenta, and wherein a capsule membrane attachment rating of moderate to little separation between the membrane and placenta is observable.

28. The plant of claim 20, wherein said membrane is situated adjacent to said placenta, and wherein a capsule membrane attachment rating of moderate to little separation between the membrane and placenta is observable.

29. A non-dehiscent sesame plant, wherein said plant is selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398, respectively.

30. A progeny plant from a non-dehiscent sesame parent plant, wherein said parent plant is selected from the group consisting of Sesaco 22, Sesaco 23, Sesaco 24, 19A, and 11W representative seed of said Sesaco 22, Sesaco 23, Sesaco 24, 19A, and 11W having been deposited under ATCC accession number PTA-1400, PTA-1401, PTA-1402, PTA-1399, and PTA-1398, respectively.

31. Seeds produced by a non-dehiscent sesame plant, wherein said plant is selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 respectively.

32. A progeny plant from seeds produced by a non-dehiscent sesame parent plant, wherein said parent plant is selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 repsetively.

33. A non-dehiscent sesame plant which can be classified into the same phenotype group characterized by a capsule opening of slightly to barely open and moderate to good capsule placenta attachment as a plant of a sesame line selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 repsetively.

34. A progeny plant from a non-dehiscent sesame parent plant wherein said parent can be classified into the same phenotype group characterized by a capsule opening of slightly to barely open and moderate to good capsule placenta attachment as a plant of a sesame line selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 respectively.

35. Seeds produced by a non-dehiscent sesame plant which can be classified into the same phenotype group characterized by a capsule opening of slightly to barely open and moderate to good capsule placenta attachment as a plant of a sesame line selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 respectively.

36. A progeny plant from seeds produced by a non-dehiscent sesame parent plant wherein said parent plant can be classified into the same phenotype group characterized by a capsule opening of slightly to barely open and moderate to good capsule placenta attachment as a plant of a sesame line selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA1399, and PTA-1398 respectively.

37. A method of breeding non-dehiscent sesame plants comprising the steps of:

a) crossing a first parental plant having a capsule opening of slightly to barely open with a second parental plant having moderate to good capsule placenta attachment;

b) recovering F1 plants;

c) selfing F1 plants to produce F2 plants; and d) selecting said F2 plants having phenotypic characteristics of a capsule opening of slightly to barely open and a moderate to good capsule placenta attachment.

38. The method of claim 37, wherein said F2 plants express the non-dehiscent phenotype characterized by a capsule opening of slightly to barely open and moderate to good capsule placenta attachment as a plant of a sesame line selected from the group consisting of Sesaco 22, Sesaco 23, Sesaco 24, 19A, and 11W, representative seed of said Sesaco 22, Sesaco 23, Sesaco 24, 19A, and 11W having been deposited under ATCC accession number PTA-1400, PTA-1401, PTA-1402, PTA-1399, and PTA-1398 respectively.

39. Seed produced from F2 plants produced according to a method of breeding non-dehiscent sesame plants comprising the steps of:

a) crossing a first parental plant having a capsule opening of slightly to barely open with a second parental plant having moderate to good capsule placenta attachment:

b) recovering F1 plants:

c) selfing F1 plants to produce said F2 plants; and d) selecting said F2 plants having phenotypic characteristics of a capsule opening of slightly to barely open and a moderate to good capsule placenta attachment.

40. A progeny plant produced from seeds produced from F2 plants produced according to a method of breeding non-dehiscent sesame plants comprising the steps of:

a) crossing a first parental plant having a capsule opening of slightly to barely open with a second parental plant having moderate to good capsule placenta attachment;

b) recovering F1 plants:

c) selfing F1 plants to produce said F2 plants; and d) selecting said F2 plants having phenotypic characteristics of a capsule opening of slightly to barely open and a moderate to good capsule placenta attachment.

41. A progeny plant produced according to a method of breeding non-dehiscent sesame plants comprising the steps of:

a) crossing a first parental plant having a capsule opening of slightly to barely open with a second parental plant having moderate to good capsule placenta attachment; and b) recovering F1 plants;

wherein said progeny plant is an F1 plant.

42. Seed produced from F2 plants produced according to a method of breeding non-dehiscent sesame plants comprising the steps of:

a) crossing a first parental plant having a capsule opening of slightly to barely open with a second parental plant having moderate to good capsule placenta attachment;

b) recovering F1 plants;

c) selling F1 plants to produce said F2 plants; and d) selecting said F2 plants having phenotypic characteristics of a capsule opening of slightly to barely open and moderate to good capsule placenta attachment, wherein said F2 plant can be classified into the same phenotype group characterized by a capsule opening of slightly to barely open and moderate to good capsule placenta attachment selected from the group consisting of Sesaco 22, Sesaco 23, Sesaco 24, 19W, and 11W, representative seed of Sesaco 22, Sesaco 23, Sesaco 24, 19W, and 11W having been deposited under ATCC accession number PTA-1400, PTA-1401, PTA-1402, PTA-1399, and PTA-1398, respectively.

43. A progeny plant produced from seeds produced from F2 plants produced according to a method of breeding non-dehiscent sesame plants comprising the steps of:

a) crossing a first parental plant having a capsule opening of slightly to barely open with a second parental plant having moderate to good capsule placenta attachment;

b) recovering F1 plants;

c) selfing F1 plants to produce said F2 plants; and d) selecting said F2 plants having phenotypic characteristics of a capsule opening of slightly to barely open and moderate to good capsule placenta attachment, wherein said F2 plant can be classified into the same phenotype group characterized by a capsule opening of slightly to barely open and moderate to good capsule placenta attachment selected from the group consisting of Sesaco 22, Sesaco 23, Sesaco 24, 19W, and 11W, representative seed of Sesaco 22, Sesaco 23, Sesaco 24, 19W, and 11W having been deposited under ATCC accession number PTA-1400, PTA-1401, PTA-1402, PTA-1399, and PTA-1398, respectively.

44. An F2 progeny plant produced according to a method of breeding non-dehiscent sesame plants comprising the steps of:

a) crossing a first parental plant having a capsule opening of slightly to barely open with a second parental plant having moderate to good capsule placenta attachment;

b) recovering F1 plants;

c) selfing F1 plants to produce said F2 plants; and d) selecting said F2 plants having phenotypic characteristics of a capsule opening of slightly to barely open and moderate to good capsule placenta attachment, wherein said progeny plant can be classified into the same phenotype group characterized by a capsule opening of slightly to barely open and moderate to good capsule placenta attachment at the top of the capsule as a plant of a sesame line selected from the group consisting of Sesaco 22, Sesaco 23, Sesaco 24, 19W, and 11W, representative seed of Sesaco 22, Sesaco 23, Sesaco 24, 19W, and 11W having been deposited under ATCC accession number PTA-1400, PTA-1401, PTA-1402, PTA-1399, and PTA-1398, respectively.

45. A method of screening for sesame plant varieties having non-dehiscence which comprises the steps of:

a) removing a representative number of capsules from said sesame plant;

b) shaking a container holding said capsules with a mechanical shaker at an effective mechanical force to dislodge sesame seed from said capsules at a rate approximating the rate determined by dividing the weight of seed manually removed from representative capsules harvested from sesame plants left in the field for three months after initial drydown by the weight of seed manually removed from representative capsules harvested from sesame plants at initial drydown;

c) quantitating the amount of sesame seed dislodged by shaking;

d) quantitating the amount of sesame seed retained in said capsules after shaking;

e) adding the amount of sesame seed dislodged by shaking and the amount of sesame seed retained in said capsules to determine the total amount of sesame seed in capsules; and f) quantitatively comparing the amount of sesame seed retained by shaking to the total amount of sesame seed in capsule;

said sesame plant varieties having non-dehiscence if said sesame seed retained in said capsule after shaking is from about 65% to about 100% of said total amount of sesame seed in capsule.

46. A sesame plant which passes the test according to a method of screening for sesame plant varieties having non-dehiscence which comprises the steps of:

a) removing a representative number of capsules from said sesame plant;

b) shaking a container holding said capsules with a mechanical shaker at an effective mechanical force to dislodge sesame seed from said capsules at a rate approximating the rate determined by dividing the weight of seed manually removed from representative capsules harvested from sesame plants left in the field for three months after initial drydown by the weight of seed manually removed from representative capsules harvested from sesame plants at initial drydown;

c) quantitating the amount of sesame seed dislodged by shaking;

d) quantitating the amount of sesame seed retained in said capsules after shaking;

e) adding the amount of sesame seed dislodged by shaking and the amount of sesame seed retained in said capsules to determine the total amount of sesame seed in capsules; and f) quantitatively comparing the amount of sesame seed retained by shaking to the total amount of sesame seed in capsule;

said sesame plant varieties having non-dehiscence if said sesame seed retained in said capsule after shaking is from about 65% to about 100% of said total amount of sesame seed in capsule.

* * * * *